United States Patent [19]

Ryan

[11] Patent Number: 5,154,699
[45] Date of Patent: Oct. 13, 1992

[54] SAFETY WINGED NEEDLE DEVICE FOR USE WITH FISTULAS

[75] Inventor: Dana W. Ryan, Franklin, Tenn.

[73] Assignee: Ryan Medical, Inc., Brentwood, Tenn.

[21] Appl. No.: 551,142

[22] Filed: Jul. 11, 1990

Related U.S. Application Data

[63] Continuation-in-part of Ser. No. 162,569, Mar. 1, 1988, Pat. No. 5,059,185, Ser. No. 257,407, Oct. 13, 1988, Pat. No. 5,088,982, Ser. No. 303,588, Jan. 27, 1989, Pat. No. 5,067,945, Ser. No. 416,927, Oct. 4, 1989, Pat. No. 5,085,639, and Ser. No. 520,239, May 7, 1990, Pat. No. 5,066,287.

[51] Int. Cl.$^5$ ............................................. A61M 5/00
[52] U.S. Cl. ................................... 604/116; 604/192; 604/198; 604/263; 128/763
[58] Field of Search ............... 604/116, 162, 177, 192, 604/194–198, 240–243, 263, 111, 181, 188, 187, 199, 211, 212, 214, 216, 232, 329, 174, 186, 171, 268; 128/760, 762–767, 776, DIG. 26

[56] References Cited

U.S. PATENT DOCUMENTS

| | | |
|---|---|---|
| 1,757,680 | 5/1930 | Neil . |
| 2,273,211 | 2/1942 | Martinet . |
| 2,290,857 | 7/1942 | Booye et al. . |
| 2,571,653 | 10/1951 | Bastien . |
| 2,587,717 | 3/1952 | Fourness . |
| 2,725,058 | 11/1955 | Rathkey . |
| 2,740,404 | 4/1956 | Kohl . |
| 2,847,995 | 8/1958 | Adams . |
| 2,888,923 | 6/1959 | Da Cunha Reis . |
| 2,888,924 | 6/1959 | Dunmire . |
| 2,925,083 | 2/1960 | Craig . |
| 3,021,942 | 2/1962 | Hamilton . |
| 3,043,304 | 7/1962 | Higgins . |
| 3,046,985 | 7/1962 | Saenz . |
| 3,055,361 | 9/1962 | Ballard . |
| 3,064,648 | 11/1962 | Bujan . |
| 3,073,301 | 1/1963 | Linder . |
| 3,148,680 | 9/1964 | Roberts et al. . |
| 3,150,661 | 9/1964 | Maki . |

(List continued on next page.)

FOREIGN PATENT DOCUMENTS

| | | |
|---|---|---|
| 0186232 | 7/1986 | European Pat. Off. . |
| 528471 | 5/1939 | United Kingdom . |
| 2183484A | 6/1987 | United Kingdom . |

*Primary Examiner*—Randall L. Green
*Assistant Examiner*—K. Reichle
*Attorney, Agent, or Firm*—David P. Gordon

[57] ABSTRACT

Shielded winged needled medical devices for use as part of fistula sets and which minimize accidental needlesticks of the skin by an exposed contaminated needle are provided. The medical devices include a hollow inner tube body, and a sliding hollow outer winged shield. The inner tube has a foward groove and a ratcheted rear groove on the outside surface thereof, a shoulder of relatively large diameter forwardly adjacent the front groove, and a ramp of diameter smaller than the shoulder rearwardly adjacent the front groove. The outer shield has an inner surface with first and second ramps and a ratcheted protrusion which terminates the second ramp. The ratcheted protrusion sits in the ratcheted rear groove of the inner tube while the winged needle device is being used and eliminates inadvertent rotation while permitting forced rotation at any time between the inner tube and outer shield. After use, the outer shield may be slid forward relative to the inner tube, overcoming resistance given by the engagement of the protrusion and a ramp forward the rear groove, until the protrusion slides up the ramp rearwardly adjacent the front groove and locks in the forward groove. In this forward position, the now-contaminated needle is shielded, with the ramps, grooves, and shoulder of the inner tube and outer shield providing an absolute lock which may not be overcome by manual force.

30 Claims, 3 Drawing Sheets

U.S. PATENT DOCUMENTS

| | | |
|---|---|---|
| 3,304,934 | 2/1967 | Bautista . |
| 3,306,290 | 2/1967 | Weltman . |
| 3,314,428 | 4/1967 | Johnson et al. . |
| 3,329,146 | 7/1967 | Waldman, Jr. . |
| 3,356,089 | 12/1967 | Francis . |
| 3,469,581 | 9/1969 | Burke . |
| 3,487,834 | 1/1970 | Smith, Jr. et al. . |
| 3,491,757 | 1/1970 | Arce . |
| 3,494,351 | 2/1970 | Horn . |
| 3,494,392 | 2/1970 | Russo et al. . |
| 3,536,073 | 10/1970 | Farb . |
| 3,572,334 | 3/1971 | Petterson . |
| 3,640,275 | 2/1972 | Burke et al. . |
| 3,658,061 | 4/1972 | Hall . |
| 3,670,727 | 6/1972 | Reiterman . |
| 3,721,241 | 3/1973 | Klohr et al. . |
| 3,734,080 | 5/1973 | Petterson et al. . |
| 3,769,975 | 11/1973 | Nimoy et al. . |
| 3,780,734 | 12/1973 | Wulff . |
| 3,782,383 | 1/1974 | Thompson . |
| 3,848,579 | 11/1974 | Villa-Real . |
| 3,874,367 | 4/1975 | Ayres . |
| 3,877,465 | 4/1975 | Miyake . |
| 3,886,930 | 6/1975 | Ryan . |
| 3,890,971 | 6/1975 | Leeson et al. . |
| 3,906,930 | 9/1975 | Guerra . |
| 3,906,946 | 9/1975 | Nordstrom . |
| 3,910,272 | 10/1975 | Forberg . |
| 3,930,499 | 1/1976 | Rimbaud . |
| 4,015,600 | 4/1977 | Liautaud . |
| 4,026,287 | 5/1977 | Haller . |
| 4,085,737 | 4/1978 | Bordow . |
| 4,116,196 | 9/1978 | Kaplan et al. . |
| 4,139,009 | 2/1979 | Alvarez . |
| 4,140,108 | 2/1979 | Nugent . |
| 4,140,127 | 2/1979 | Cianci et al. . |
| 4,160,450 | 7/1979 | Doherty . |
| 4,168,699 | 9/1979 | Hauser . |
| 4,170,993 | 10/1979 | Alvarez . |
| 4,186,745 | 2/1980 | Lewis et al. . |
| 4,237,882 | 12/1980 | Wickham . |
| 4,266,543 | 5/1981 | Blum . |
| 4,273,123 | 6/1981 | Lemelson . |
| 4,281,653 | 8/1981 | Barta et al. . |
| 4,349,022 | 9/1982 | Ishikawa . |
| 4,356,822 | 11/1982 | Winstead-Hall . |
| 4,362,156 | 12/1982 | Feller, Jr. et al. . |
| 4,366,817 | 1/1983 | Thomas . |
| 4,373,526 | 2/1983 | Kling . |
| 4,383,530 | 5/1983 | Bruno . |
| 4,392,856 | 7/1983 | Lichtenstein . |
| 4,411,647 | 10/1983 | Sakurai et al. . |
| 4,411,656 | 10/1983 | Cornett, III . |
| 4,417,887 | 11/1983 | Koshi . |
| 4,419,098 | 12/1983 | Bennett . |
| 4,425,120 | 1/1984 | Sampson et al. . |
| 4,479,791 | 10/1984 | Sprague . |
| 4,485,918 | 12/1984 | Mayer . |
| 4,507,117 | 6/1985 | Vining et al. . |
| 4,559,042 | 12/1985 | Votel . |
| 4,568,336 | 2/1986 | Cooper . |
| 4,573,975 | 3/1986 | Frist et al. . |
| 4,573,976 | 3/1986 | Sampson et al. . |
| 4,576,671 | 3/1986 | Shimanaka . |
| 4,592,744 | 6/1986 | Jagger et al. . |
| 4,596,562 | 6/1986 | Vernon . |
| 4,610,667 | 9/1986 | Pedicano . |
| 4,611,382 | 9/1986 | Clark . |
| 4,613,326 | 9/1986 | Szwarc . |
| 4,623,336 | 11/1986 | Pedicano . |
| 4,627,842 | 12/1986 | Katz . |
| 4,629,453 | 12/1986 | Cooper . |
| 4,631,057 | 12/1986 | Mitchell . |
| 4,639,249 | 1/1987 | Larson . |
| 4,643,199 | 2/1987 | Jennings, Jr. . |
| 4,643,200 | 2/1987 | Jennings, Jr. et al. . |
| 4,643,722 | 2/1987 | Smith, Jr. . |
| 4,650,468 | 3/1987 | Jennings, Jr. . |
| 4,654,034 | 3/1987 | Masters et al. . |
| 4,655,751 | 4/1987 | Harbaugh . |
| 4,659,330 | 4/1987 | Nelson et al. . |
| 4,664,128 | 5/1987 | Lee . |
| 4,664,259 | 5/1987 | Landis . |
| 4,664,654 | 5/1987 | Strauss . |
| 4,666,435 | 5/1987 | Braginetz . |
| 4,675,005 | 6/1987 | DeLuccia . |
| 4,676,783 | 1/1987 | Jagger et al. . |
| 4,681,567 | 7/1987 | Masters et al. . |
| 4,690,675 | 9/1987 | Katz . |
| 4,693,708 | 9/1987 | Wanderer et al. . |
| 4,702,738 | 10/1987 | Spencer . |
| 4,702,739 | 10/1987 | Milorad . |
| 4,713,056 | 12/1987 | Butterfield . |
| 4,720,285 | 1/1988 | Pickhard . |
| 4,723,943 | 2/1988 | Spencer . |
| 4,726,805 | 2/1988 | Sanders, III . |
| 4,735,311 | 4/1988 | Lowe et al. . |
| 4,737,144 | 4/1988 | Choksi . |
| 4,738,603 | 4/1988 | Bogan . |
| 4,747,830 | 5/1988 | Gloyer et al. . |
| 4,747,837 | 5/1988 | Hauck . |
| 4,752,290 | 6/1988 | Schramm . |
| 4,758,231 | 7/1988 | Haber et al. . |
| 4,762,516 | 8/1988 | Luther et al. . |
| 4,767,413 | 8/1988 | Haber et al. . |
| 4,772,272 | 9/1988 | McFarland . |
| 4,778,453 | 10/1988 | Lopez . |
| 4,781,684 | 11/1988 | Trenner . |
| 4,781,692 | 11/1988 | Jagger et al. . |
| 4,790,827 | 12/1988 | Haber et al. . |
| 4,816,022 | 3/1989 | Poncy . |
| 4,820,282 | 4/1989 | Hogan . |
| 4,834,711 | 5/1989 | Greenfield . |
| 4,834,716 | 5/1989 | Ogle, II . |
| 4,838,876 | 6/1989 | Wong et al. . |
| 4,846,796 | 7/1989 | Carrell et al. . |
| 4,846,811 | 7/1989 | Vanderhoof . |
| 4,865,592 | 9/1989 | Rycroft . |
| 4,871,355 | 10/1989 | Kikkawa . |
| 4,874,384 | 10/1989 | Nunez . |
| 4,917,679 | 4/1990 | Kronner . |
| 4,923,445 | 5/1990 | Ryan . |
| 4,989,590 | 2/1990 | Andors . |
| 5,066,287 | 11/1991 | Ryan ................................ 604/240 |

SAFETY WINGED NEEDLE DEVICE FOR USE WITH FISTULAS

This application is a continuation-in-part of copending Ser. No. 07/162,569 filed Mar. 1, 1988, now U.S. Pat. No. 5,059,185 Ser. No. 07/257,407 filed Oct. 13, 1988, now U.S. Pat. No. 5,088,982 Ser. No. 07/303,588 filed Jan. 27, 1989, now U. S. Pat. No. 5,067,945 07/416,927, filed Oct. 4, 1989, now U.S. Pat. No. 5,085,639, and Ser. No. 07/520,239 filed May 7, 1992 now U.S. Pat. No. 5,066,287, all of which are hereby incorporated herein.

BACKGROUND OF THE INVENTION

The present invention generally relates to needled devices for use with fistulas for hemodialysis and blood collection. More particularly, the present invention relates to safety winged needled device which are designed to minimize the incidence of accidental needlesticks after contamination of a needle used in conjunction with a fistula in hemodialysis and blood collection procedures.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patient beds, linens, and in garbage cans, and place health care, housekeeping and sanitation personnel at risk. Because accidental needlesticks can now result in deadly incurable diseases as well as the previously appreciated serious, but curable diseases, the need for eliminating the needlestick problem has reached extreme urgency. In addressing the urgency, many devices have been proposed. Indeed, reference may be had to the background section of parent application hereof, U.S. Application Ser. No. 07/162,569 for a discussion of the prior art of safety needles, as well as the background section of parent application hereof, U.S. Application Ser. No. 07/257, 407 for a discussion of the prior art relating to winged needle arrangements. While many safety devices have been proposed, for various reasons, none have found even a minimal amount of acceptance in the field except for those safety devices of the applicant which are described in the parent applications hereto.

Even with all of the safety needled devices proposed in the art, none of the proposals have addressed the particularities of needles used with fistulas in hemodialysis and blood collection procedures. In particular, where fistulas (artificial veins) are used in hemodialysis, one fistula is provided on the intake side of the blood cleansing equipment, and another fistula is provided on the outgoing side. On the intake side, the fistula is subject to collapsing due to the negative pressure applied to suck the blood from the vein into the fistula, through a needle assembly and tubing, and into a hemodialysis machine. In order to reopen or prevent collapsing of the fistula, practitioners periodically rotate the needle so that the angled opening of the needle (towards which the fistula tends to collapse) is moved. The procedure of rotating the needle, however, typically requires the untaping and retaping of a winged needled device to the skin of a patient. Not only is such a procedure inconvenient, but where the wings of the winged needle device are fixed to the needle, only two positions (up and down) for the needle are available. While winged needle devices with free spinning needles are known, these devices still suffer from the requirement of fixing the needle in place relative to the wings after each rotation in order to avoid otherwise inadvertent and possibly damaging movement of the needle in the fistula.

SUMMARY OF THE INVENTION

It is therefore an object of the present invention to provide winged needle safety devices for use with fistulas which are easy and economical to manufacture and assemble, and are easy to use.

It is a further object of the invention to provide winged needle safety devices for use as part of fistula sets where the needle of the winged needle safety device may be rotated in a fistula by fixed amounts and held in place without taping or complicated procedures.

It is another object of the invention to provide winged needle safety shielded devices for use with fistulas, where the winged needle device uses a locking mechanism in which the movement of a shield from an unshielding position to a locked shielding position may be accomplished in an easy uniform sliding motion, and where the winged needle device also uses a rotational locking mechanism in which in the unshielded position, the needle is held firmly relative to a shield but may be rotated by fixed amounts without retaping procedures.

It is yet a further object of the invention to provide a winged needle safety shielded device for use as part of a fistula set where the safety device has an outer shield and an inner tube, such that in a first position, the outer shield does not shield the intravenous needle attached to the inner tube, and such that in a second position, the outer shield extends over and shields the intravenous needle while locking completely with the inner tube so as to completely prevent unintended reexposure.

In accord with the objects of the invention, a safety shielded winged needle assembly is provided and is comprised of two cooperating pieces; a hollow inner tube needle adapter, and an outer hollow shield. If desired, a hollow needle may also be provided as part of the assembly with the inner tube preferably molded around the needle. Where the inner tube is not molded around the needle, the hollow inner tube needle adapter has a front end adapted to have the hollow needle secured thereto. The hollow inner tube has an outer surface having a front shoulder of relatively large diameter. Directly behind the front shoulder is a first groove which is defined on its other side by the termination of a ramped surface which ramps downward away from the groove. The inner tube also includes a second groove which is located towards the rear of the inner tube, and which includes outwardly extending ratchet teeth which are preferably ramped so as to increase in diameter as they extend rearward. The second groove is defined on the rear end by the termination of a ramped surface which ramps downward away from the groove, and on its front end by a ramp which ramps upward away from the groove. The upward ramp is followed by a downward ramp as it extends towards the front end of the inner tube.

The outer shield is formed with an inner surface which cooperates with the outer surface of the inner tube. At the rear end of the outer shield is formed a first ramped protrusion which is used, during the shielding process, to ride over the front shoulder of the inner tube and snap-lock thereover to prevent the outer shield from being retracted thereafter. Following the first protrusion is a groove which is formed to cooperate and sit around the front shoulder of the inner tube when the shield is shielding the needle. The groove in the inner surface of the outer shield is terminated by a second ramped protrusion. The second ramped protrusion circumscribes a smaller inner diameter than the first protrusion and is arranged so that it cannot be pulled over the front shoulder of the inner tube. The second ramped protrusion is also arranged to sit in but be movable over (i.e. be removably engaged with) the rear groove of the inner sleeve. In this manner, in a first retracted (non-shielding) position the outer shield is engaged with the inner tube such that the shield does not slip off the inner tube; and in a second extended (shielding) position, the outer shield locks with the inner tube thereby covering a contaminated needle and virtually guaranteeing that the contaminated needle will not be reexposed. The second ramped protrusion further includes a ramped ratchet mechanism which cooperates with the ratchet teeth of the inner tube so as to prevent inadvertent rotation. However, the ramped ratchet mechanism and ratchet teeth of the outer shield and inner tube are arranged to permit forced rotation of one relative to other by fixed amounts (e.g. 12 degrees per click).

Other aspects of the outer shield include wings extending from its outer surface, and thumb grip ribs extending from the top of the outer surface. Other aspects of the inner tube include a rotational indicator for showing the degree of rotation between the inner tube and outer shield, and a rear extension which is ribbed on its outside for coupling to tubing. The rear extension preferably is also ramped on its inside at its termination with decreasing inner diameter as it extends towards the needle end so as to prevent turbulence for fluids flowing into the winged needle device.

A better understanding of the safety winged needle medical assembly for use with fistula sets of the invention, and additional objects and advantages of the invention will become apparent to those skilled in the art upon reference to the detailed description and accompanying drawings.

BRIEF DESCRIPTION OF THE DRAWINGS

FIGS. 1a and 1b are pan and cross-sectional views of the inner tube needle adapter of the invention;

FIG. 1c is a cross-sectional view of the inner tube needle adapter taken along line 1c—1c of FIG. 1a;

FIGS. 3a and 3b are plan and cross-sectional views of the winged shield of the invention;

FIG. 3c is a sectional view of a portion of the winged shield taken along line 3c—3c of FIG. 3a; and FIG. 3d is a rear view of the winged shield of FIG. 3a.

DETAILED DESCRIPTION OF THE PREFERRED EMBODIMENT

Turning to FIGS. 1a—1c and 2a and 2b, details of the hollow inner tube needle adapter 210 are seen. The hollow inner tube has an outer surface 242 having a front shoulder 246 of relatively large diameter. The front shoulder 246 is defined by a front face 247 and a rear abutment face 248. Extending forwardly from front face 247 is a nose 401 which has axial protrusions 403 which are used to retain a needle guard (not shown). The needle guard is removed before the winged infusion needle device is used. Directly behind the front shoulder 246 is a first groove 238 which is defined on one side by the abutment face 248 and on its other side by the termination (rear abutment face) 250 of a ramped surface 252. The ramped surface 252 starts with a diameter smaller than that of the front shoulder 246 and ramps downward away from the first groove 238. Ramp 252 terminates in a long valley defined by outer surface 242 of needle adapter 210. The valley has a relatively constant diameter which is preferably substantially equal to the diameter of the first groove 238. The valley ends in a ramp 254 which increases in diameter as it extends away from the front end of the needle adapter 210. Ramp 254 is followed by ramp 256 which ramps down to a second groove 236.

Figure 1A:
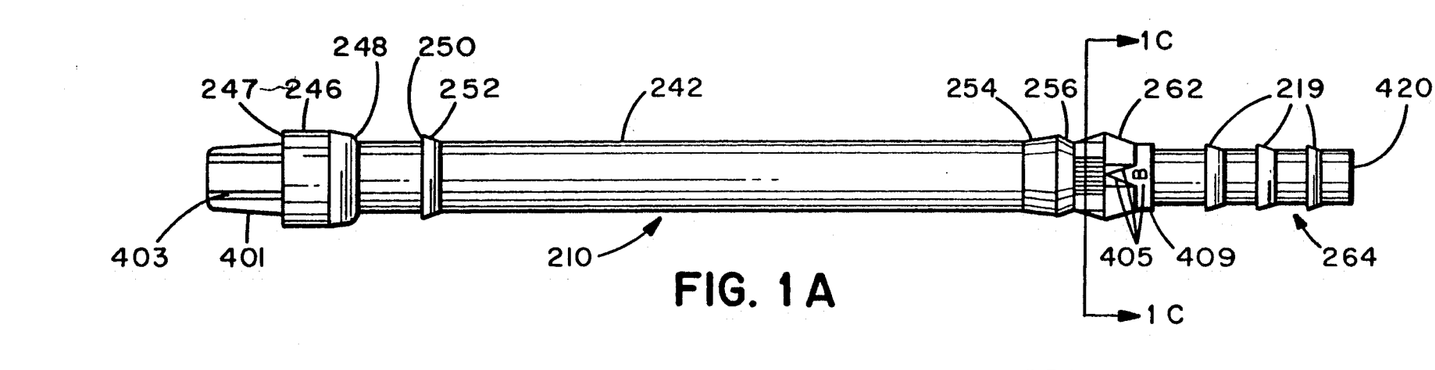

The second groove 236 contains a plurality of ratchet teeth 400 (best seen in FIG. 1c) which are preferably ramped to increase in outer diameter (see FIG. 1a) as they extend toward the rear end of the inner tube. As will be described hereinafter, the ramped teeth serve the function of preventing unintended rotation between the inner tube and the outer shield, but permit forced rotation. By having the teeth spaced at twelve degree intervals, forced rotations of twelve degrees, or multiples thereof, is permitted to help prevent collapse of a fistula. Of course, if desired, other spacings could be utilized. The root diameter of the ratcheted groove 236 is preferably of a diameter equal to, or slightly larger than the diameter of the valley 242. The ratcheted groove 236 terminates in a rear abutment surface 259 which is interrupted by the ramped teeth 400. The surface 259 is also the terminating surface of a rear ramp 262. The rear ramp 262 preferably includes a marker or indicator 405 which may take the form of marks, a notch, a raised indicator, etc. The marker 405 is provided to indicate how the inner tube 210 and the needle 300 which is fixed therein are rotated relative to the outer shield. As shown in FIG. 1a, the marker 405 includes an arrow and the letter "B" which signifies the bevel 408 of the needle 300. As shown in FIG. 1a, the letter B is located on a plateau 409 which terminates rear ramp 262.

The plateau 409 sits between the rear ramp 262 and the ribbed connecting end 264 of the needle adapter 210. The connecting end 264 has outwardly extending ribs 219 as indicated for coupling with standard tubing (not shown). The connecting end 264 preferably also includes a conically shaped inner surface 410 which increases in diameter as it extends from the end of needle 300 outward to the end 420 of the inner tube.

Figures 1B, 1C:
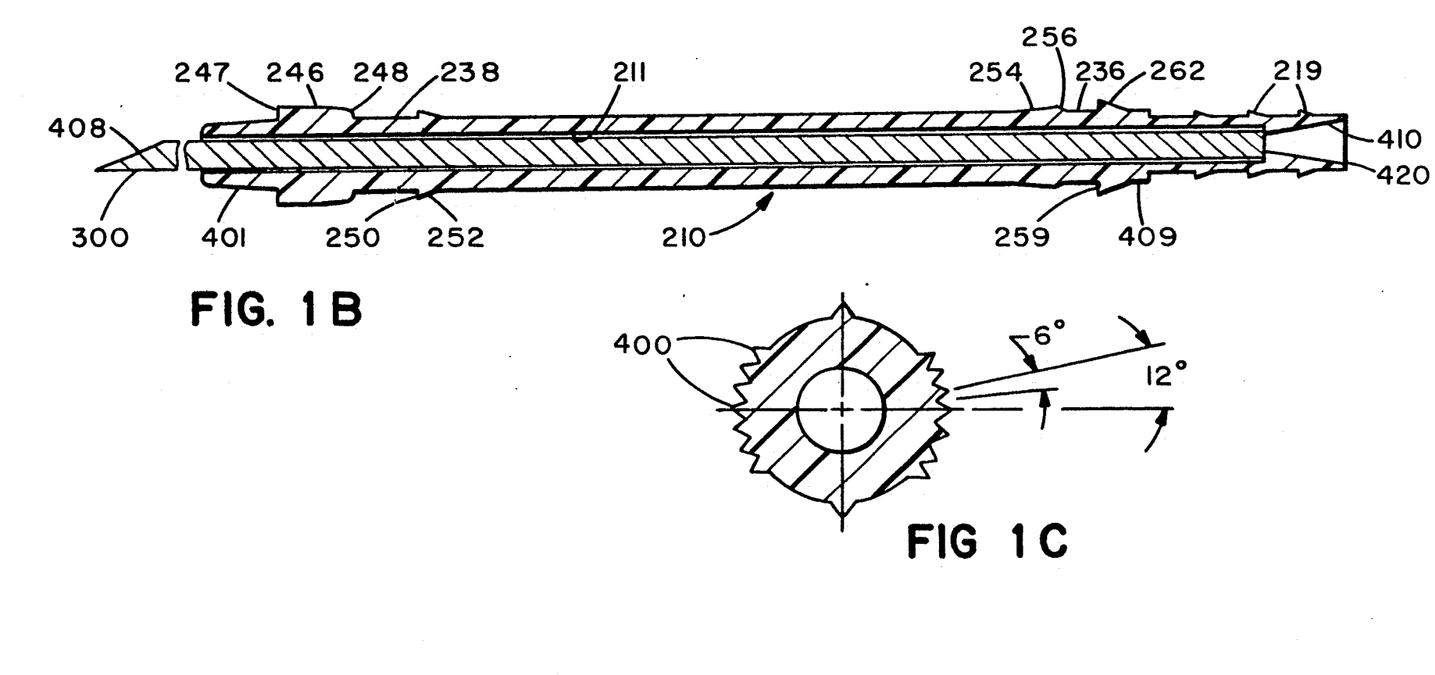

As previously indicated, the inner tube 210 is hollow. In the preferred embodiment, the inner tube 210 is formed around a needle 300 such as seen in FIG. 1b, by insert molding techniques. With such a manufacturing process, the inner surface 211 of the inner tube 210 bonds to the needle 300 to prevent relative movement therebetween. However, if desired, and as shown in the parent application hereto, U.S. Application Ser. No. 07/416,927, the inner surface can be modified so that a short needle can be inserted and glued into place.

Figures 3A, 3B, 3C, 3D:
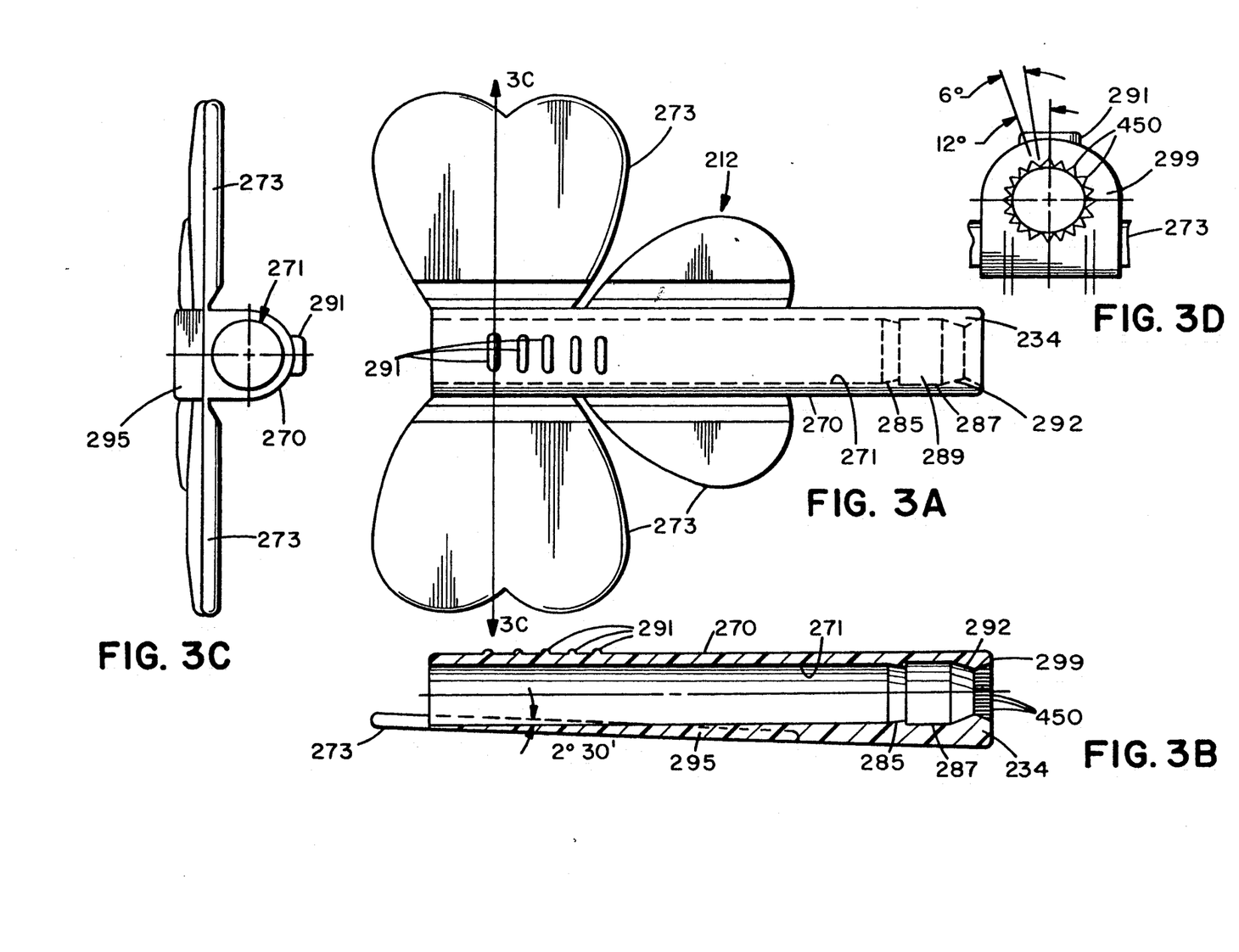

Turning to FIGS. 3a–3d, details of the outer sleeve 212 are shown. Outer sleeve 212 includes flexible wings 273 which are used as means for attachment of the winged needle device to a patient. The flexible wings 273 are attached to the outer surface 270 of the outer sleeve 212. Projecting from the top outer surface 270 of the outer sleeve 212 are thumb grips or ribs 291 which provide the practitioner with a friction surface when utilizing the winged needle device. As indicated in FIG. 3b, the outer sleeve 212 has a flat but tapered bottom surface 295 with the thickness of the bottom increasing according to a two and one half degree slope as it extends away from the front end of the outer sleeve. As a result, when the inner tube 210 and needle 300 are located in the outer sleeve, the needle assumes a downward angle preferably of about two and one half degrees, and is more easily inserted into the fistula.

Outer sleeve 212 is hollow and has an inner surface 271 of a diameter slightly larger than the outer diameter of shoulder 246 of the inner tube 210. However, towards its rear end, the inner surface of outer sleeve 212 is arranged with two ramps 285 and 292, although, if desired, ramp 285 may be replaced with a non-ramped ramped protrusion. Ramp 285 provides outer sleeve 212 with a decreasing inner diameter as it extends toward the rear end of the outer sleeve. Ramp 285 terminates in an abutment face 289 which is followed by a flat surface 287 having an inner diameter approximately equal to the outer diameter of shoulder 246 of inner tube 210. Flat surface 287 ends with ramp 292 which has also has a decreasing inner diameter as it extends toward the rear end of the outer sleeve. The inner diameter at the end of ramp 292, however, is of significantly smaller diameter than that of ramp 285 and of significantly smaller diameter than the diameter of shoulder 246. The inner surface of the outer sleeve 212 terminates in a ratcheted ramped protrusion 234 which is arranged to cooperate with the ratchet teeth 400 of the inner tube. Thus, the ratchet 450 of ramped protrusion 234 is an inward ratchet (i e. is notched) to accommodate the teeth 400 of the inner tube, with the notches increasing in root diameter as they extend rearward and away from the front of the outer sleeve 212.

Figure 2A:
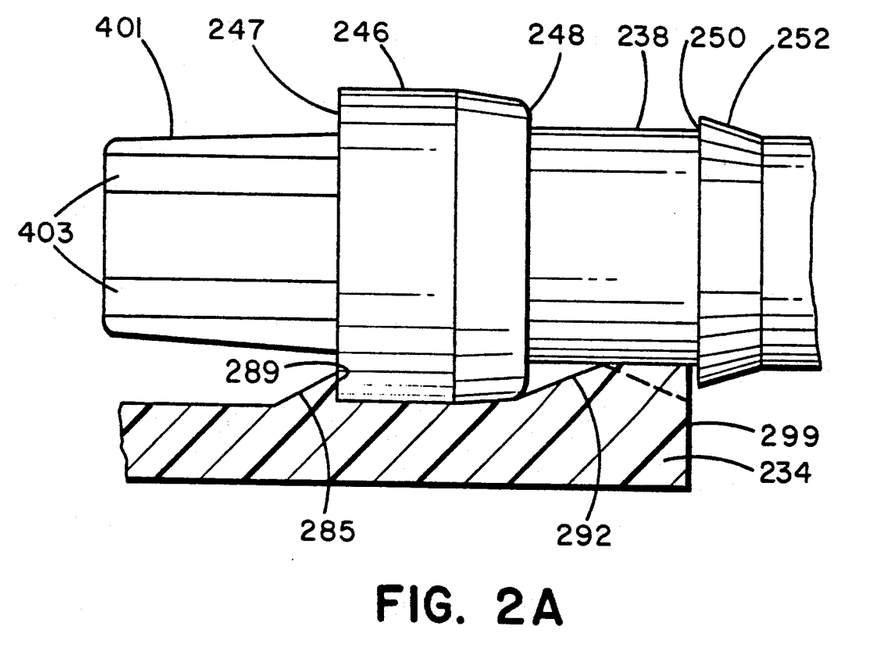
FIGS. 2a and 2b are enlarged plan views, respectively, of the front end and the back groove section of the inner tube needle adapter shown in FIG. 1a, showing the locking protrusions of the outer shield in engagement therewith.
Figure 2B:
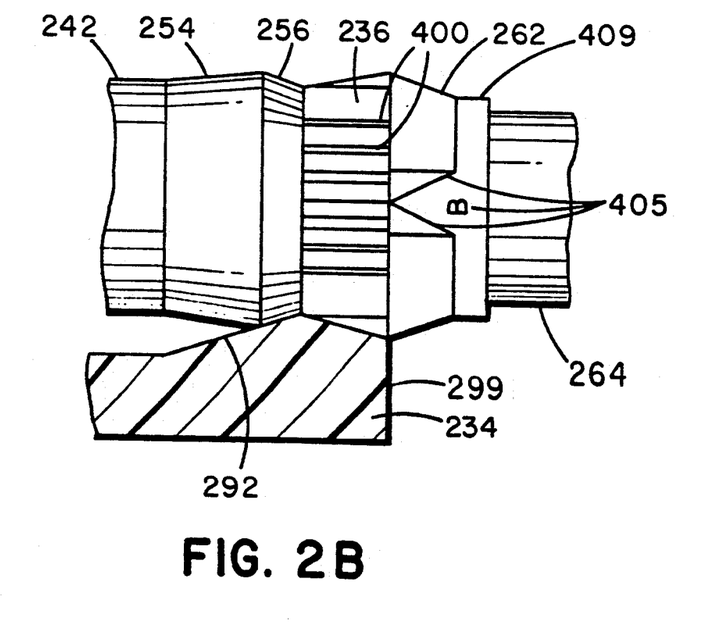

In assembling the winged needle device, the outer shield 212 and the inner tube 210 are coaxially aligned with the rear portion of the inner tube 210 at the front of the front portion of the outer sleeve 212. Relative movement between the inner tube 210 and outer sleeve 212 causes inner tube 210 to slide through outer sleeve 212 until the ratcheted ramped protrusion 234 of the outer sleeve 212 engages the ratcheted ramped groove 236 (as seen in FIG. 2b) of the inner tube, with abutment face 259 of inner tube 210 abutting the rear surface 299 of outer shield 212, with ramp 256 of inner tube 210 engaging ramp 292 of outer sleeve 212, and with ratchet teeth 400 of the inner tube engaged in notches 450 of the outer shield 212. In the assembled position, the ramp 256 of the inner tube 210 in conjunction with protrusion 234 of the outer shield 212 serves to hold the outer shield in its retracted position (i.e. prevents inadvertent forward movement of the shield) during use of the winged needle assembly. On the other hand, the abutment face 259 of the inner tube 210 in conjunction with protrusion 234, serves to keep the inner tube from sliding backward and out of assembly. At the same time, the seating of the ratchet teeth 400 of the ratcheted ramped groove 236 of the inner tube into the ratchet notches 450 of the ratcheted ramped protrusion 234 of the outer shield serves to prevent inadvertent or undesired rotation of the inner tube 210 relative to the outer shield 212.

In use, the winged needle assembly including an intravenous needle 300 is held by the practitioner with the wings 273 being squeezed upwards against the outer surface 270 of the outer sleeve 212. The practitioner then inserts the needle 300 into a fistula. After insertion, the needled device is rested on the arm or body of the patient, and the flexible wings 273 may be used as a taping surface such that the needled device may be taped to the patient. Should the fistula into which the needle 300 is inserted collapse, or be in danger of collapsing, the practitioner at any time may rotate the needle in the fistula by holding the outer shield 212 in place and by grasping and outer shield 212 in place. Depending on the angular arrangement of the ratchet teeth 400 and notches 450, the needle 300 may be rotated by desired amounts. With the ratchet teeth and notches of the preferred embodiment, rotation may be effected in twelve degree increments. Each respective forcing of the teeth over the notches preferably provides an audible click, while marker 405 provides a visual indication of the rotation of the needle relative to the outer shield 212. Thus, if it is desired to rotate the needle by approximately ninety degrees, either seven or eight clicks (84 or 96 degrees) should occur. Regardless, the same rotation procedure may be used over and over again with varying degrees of rotation if desired.

When treatment is completed and it is desired to remove the contaminated needle from the fistula, either of two procedures may be utilized to shield the needle. In one procedure, the tape is removed from the arm of the patient and the winged needle device removed. Holding the outer sleeve 212 in one hand such as with thumb on grips 291 and forefinger on bottom surface 295, and gripping the tube (not shown) extending from the ribbed end 264 of the inner tube 210 in the other hand, the inner tube 210 is pulled back relative to the outer shield 212 until positive locking is obtained as shown in FIG. 2a. In a second procedure, before the tape is removed, a finger of the practitioner is placed preferably on the top outer surface of the outer sleeve 212, while the ribbed end 264 of the inner tube 210 (with attached tube—not shown) are gripped with other fingers of the same or a different hand. The inner tube is then pulled back relative to the outer shield until positive locking is obtained, thereby withdrawing the needle from the vein and immediately shielding it in the safety device.

Regardless of the procedure used, in pulling the inner tube back relative to the outer sleeve, some minor initial force is required to overcome resistance of protrusion 234 sliding over ramp 256. However, once the protrusion slides over ramp 256, little force is needed to continue sliding the outer shield over the valley of the inner tube. Extremely minor resistance is encountered when ramp 252 of the inner tube encounters ramp 285 of the outer sleeve. More resistance, however, is encountered when ramp (or protrusion) 285 encounters shoulder 246. With the application of differential force, and due to the ramped nature of ramp 285 and the rounding of the edge of shoulder 246, ramp 285 is slid over shoulder 246 until it snaps over the shoulder 246 with abutment face 289 of the outer shield 212 in contact with abutment surface 247 of the inner tube shoulder. At the same time, protrusion 234 sits in first groove 238 with the rear surface 299 of the outer sleeve abutting abutment surface 250 of the inner tube, and shoulder 246 contacts surface 287. In this locked position, the needle is shielded entirely and securely by the outer shield 212. Two locking interactions are established (surface 289 against shoulder 246, and end surface 299 against surface 250) as seen in FIG. 2a to prevent the movement of the inner tube forward and the reexposing of the needle, while the relative sizes of the protrusion 234 and the shoulder 246 prevent any possibility of the outer shield 212 being pulled forward off of the inner tube 210.

In order for the winged needle assembly to function such that locking in the shielded position is irreversible but such that the inner tube can be assembled into an unshielded position which is not inadvertently upset, certain relative diameters and lengths between grooves, ramps, etc. of the inner tube and outer shield are desirable. Preferred dimensions are set forth in the parent application hereto U.S. patent application Ser. No. 07/416,927. Also, in order for the ramped ratchet teeth 400 of the inner tube to properly engage and function with the ramped ratcheted protrusion of the outer shield, certain relative diameters and angles are desired. For example, the root diameter of ratchet teeth 400 is preferably 0.146 inches, while the ratchet teeth 400 at their largest (i.e. at stop face 259), have a diameter of 0.168 inches. The slope of the ratchet teeth ramp is preferably approximately ten and one-half degrees. Similarly, the inner diameter of the ramped ratcheted protrusion 234 at its narrowest is 0.148 inches, while the diameter of the notches at their widest is 0.169 inches. The slope at which the notches expand is preferably the same as the slope of the ratchet teeth ramp. Also, while only fourteen ratchet teeth 400 are shown in FIG. 1c so as to reduce the amount of force required to rotate the inner tube in the outer shield, it will be appreciated that fewer or more teeth could be provided.

With the preferred dimensions, and using an inner tube made of a polyurethane/polycarbonate blend (sold under the trademark "Texin" 4210M by Mobay, Inc.) and an outer shield made of a combination of polypropylene (70% by weight) and kraton (30% by weight), rotation of the inner tube and needle relative to the outer shield is possible with the exertion of a little force, although inadvertent rotation will not occur. Also, with the preferred dimensions and materials, once the shield is locked in the shielding position, it is virtually impossible to force relative movement between the inner tube and outer shield which would reexpose the contaminated needle.

There has been described and illustrated herein safety winged needle devices for use as part of a fistula set in blood collection and hemodialysis. While particular embodiments of the invention have been described, it is, not intended that the invention be limited thereby, as it is intended that the invention be as broad in scope as the art will allow. Thus, while exact dimensions of several aspects of the inner tube and the winged outer shield of the invention were provided to show a preferred embodiment, it will be recognized that other dimensions could be utilized. Similarly while particular materials and weight percentages were described, other materials and/or percentages could be utilized. Also, while the locations along the inner tube and winged shield of particular elements of the invention were described, it will be appreciated that those locations are not necessarily fixed. For example, while the ratchet mechanism for preventing accidental rotation, but permitting desired rotation of the inner tube relative to the outer shield was described as being located at the rear ends of the inner tube and outer shield, it will be appreciated that a similar mechanism could be located at the front ends of the components; although such an arrangement is not preferred because of possible resulting torque problems. Similarly, the thumb grips, while shown at towards the front end of the outer shield, could be located more centrally or towards the rear if desired. Therefore, it will be apparent to those skilled in the art that yet other changes and modifications may be made to the invention as described without departing from the scope of the invention as so claimed.

I claim:
1. A medical device for assembly with a hollow needle, comprising:
  a) an inner tube member having
    a passageway therethrough,
    a front end through which the hollow needle is adapted to extend,
    a rear end with said passageway extending therethrough,
    an outer surface having a circumferential first groove, a shoulder forwardly adjacent said first groove and a first inner tube ramp rearwardly adjacent said first groove, a first end of said first inner tube ramp being located at said first groove and constituting a first abutment surface, said first inner tube ramp decreasing in circumference as it extends towards said rear end, wherein said shoulder circumscribes a larger cross-section area through said inner tube member than said first inner tube ramp, and said shoulder terminates at its front end in a second abutment surface, and
    a first ratchet means disposed along said outer surface of said inner tube member; and
  b) a resiliently flexible hollow outer shield member having
    an inner surface, most of said inner surface subscribing a slightly larger cross-section than most of said outer surface of said inner tube member,
    a front end having a substantially unrestricted opening therein for permitting said inner tube member to be loaded therethrough during assembly of said medical device.
    at least one winged member attached to and flexibly extending outwardly from said shield member,
    a rear end having an opening therein,
    first and second ramps located towards said rear end of said outer shield member, extending inwardly from said inner surface of said outer shield member, and subscribing smaller cross-sectional areas as they extend toward said rear end, said first ramp being forward of said second ramp and terminating in a third abutment surface, said second ramp terminating in a protrusion, said first ramp at said third abutment surface subscribing a substantially larger diameter than said second ramp at said protrusion, and
    a second ratchet means disposed along said inner surface of said shield member,
    wherein the cross-sectional area circumscribed by said protrusion of said outer shield member is substantially smaller than the circumference of said shoulder of said inner tube member, and
    said first and second ratchet means are arranged along said inner tube and shield member such that when said shield member is in a retracted position relative to said inner tube, said first ratchet means engages said second ratchet means and prevents inadvertent rotation but permits forced rotation of said inner tube relative to said out shield, and wherein when said outer shield member is in locking engagement with said inner tube member, said third abutment surface is forward of said second abutment surface, said shoulder engages said inner surface of said outer shield member between said first and second ramps, and said first abutment surface is rearward of said rear end of said shield member such that attempted movement of said inner tube member forward relative to said outer shield member is stopped by abutment of said first abutment surface and the rear end of said outer shield member, and by abutment of said second and third abutment surfaces, and attempted movement of said inner tube member backward relative to said outer shield member is stopped by abutment of said said shoulder of said inner tube member and said second ramp of said outer shield member.

2. A medical device according to claim 1, wherein: said outer surface of said inner tube member further includes a second groove rearward of said circumferential first groove.

3. A medical device according to claim 2, wherein: said first ratchet means is disposed in said second groove, and said second ratchet means is disposed at said protrusion.

4. A medical device according to claim 3, wherein: said first ratchet means includes a plurality of ratchet teeth, and said second ratchet means comprises notches.

5. A medical device according to claim 3, wherein: said first ratchet means includes a plurality of ramped ratchet teeth which increase in diameter as they extend toward said rear end of said inner tube member, and
said second ratchet means comprises ramped notches in said protrusion, where said ramped notches increase in diameter as they extend toward said rear end of said shield member.

6. A medical device according to claim 5, wherein: said first ramp of said outer shield member and said shoulder of said inner tube member are sized such that said first ramp engages but slides over said shoulder when differential force is applied between said outer shield member and said inner tube member.

7. A medical device according to claim 6, wherein: said ramped notched protrusion of said outer shield member and said shoulder of said inner tube member are sized such that said ramped notched protrusion cannot slide over said shoulder when differential force is applied is applied between said outer shield member and said inner tube member by hand.

8. A medical device according to claim 7, wherein: said second groove with said ramped ratchet teeth is located substantially toward the rear end of said inner tube member, and said second groove terminates at its front end in a second inner tube ramp increasing in circumference as it extends towards the front end of said inner tube member, and terminating at its rear end in a fourth abutment surface, such that in a retracted position, said ramped ratcheted protrusion disengageably engages said second groove.

9. A medical device according to claim 8, wherein: said second inner tube ramp terminates at its front end at a third inner tube ramp which decreases in circumference as it extends towards the front end of said inner tube, said third inner tube ramp terminating in a valley which is of reduced circumference relative to and which lies between said first and third inner tube ramps.

10. A medical device according to claim 8, wherein: in said retracted position, said second ramp of said outer shield member engages said second inner tube ramp, and said fourth abutment surface extends beyond the rear end opening of said outer shield member so as to prevent accidental disengagement of said ramped ratcheted protrusion from said second groove.

11. A medical device according to claim 1, wherein: said first ramp of said outer shield member and said shoulder of said inner tube member are sized such that said first ramp engages but slides over said shoulder when differential force is applied between said outer shield member and said inner tube member.

12. A medical device according to claim 11, wherein: said protrusion of said outer shield member and said shoulder of said inner tube member are sized such that said protrusion cannot slide over said shoulder when differential force is applied between said outer shield member and said inner tube member by hand.

13. A medical device according to claim 12, wherein: said second groove is located substantially toward the rear end of said inner tube member, and said second groove terminates at its front end in a second inner tube ramp increasing in circumference as it extends towards the front end of said inner tube member, and terminating at its rear end in a fourth abutment surface, such that in a retracted position, said protrusion disengageably engages said second groove.

14. A medical device according to claim 13, wherein: said second inner tube ramp terminates at its front end at a third inner tube ramp which decreases in circumference as it extends towards the front end of said inner tube, said third inner tube ramp terminating in a valley which is of reduced circumference relative to and which lies between said first and third inner tube ramps.

15. A medical device according to claim 13, wherein: in said retracted position, said second ramp of said outer shield member engages said second inner tube ramp, and said fourth abutment surface extends beyond the rear end opening of said outer shield member so as to prevent accidental disengagement of said protrusion from said second groove.

16. A medical device according to claim 1, wherein: said outer shield member includes an outer surface with a substantially flat surface.

17. A medical device according to claim 16, wherein: said substantially flat surface is angled relative to a portion of said passageway of said inner tube member by an angle of less than ten degrees.

18. A medical device according to claim 2, wherein: said angle of less than ten degrees is between two and three degrees.

19. A medical device according to claim 1, further comprising:
c) a hollow needle extending in said passageway and terminating on one end forward of said front end of said inner tube member.

20. A medical device according to claim 19, wherein:

said inner tube member is molded around said hollow needle.

21. A medical device for assembly with a hollow needle having a sharp end, comprising:
a) an inner tube member having
a passageway therethrough,
a front end through which the hollow needle is adapted to extend
a rear end through which said passageway extends, and
an outer surface with first locking means and with first rotation control means; and
b) a resiliently flexible hollow outer shield member having
a front end having a substantially unrestricted opening therein for permitting said inner tube member to be loaded therethrough during assembly of said medical device, outwardly from said shield member,
a rear end having an opening therein, and
an inner surface with second locking means and with second rotation control means, wherein
said first locking means and second locking means comprise means for engaging said inner tube member and said outer shield member in a locked shielding position with said outer shield member surrounding and shielding the hollow needle such that said outer shield member cannot be substantially moved forward or backward relative to said inner tube member so as to reexpose the sharp end of the hollow needle through use of manual force on said inner tube member and said outer shed member, and
said first rotation control means and second rotation control means comprise means for engaging said inner tube member and said outer shield member in a retracted position such that the inner tube member cannot be inadvertently rotated but can be forcibly rotated relative to said outer tube member by desired amounts, and
in said retracted position, said outer shield member at least partially surrounds said inner tube member, and the sharp end of the needle is exposed.

22. A medical device according to claim 21, wherein:
said first rotation control means comprises ratchet teeth disposed along said outer surface of said inner tube member, and said second rotation control means comprises ratchet notches in and disposed along said inner surface of said outer shield member.

23. A medical device according to claim 22 wherein:
said first locking means is comprised of a circumferential first groove, a shoulder forwardly adjacent said first groove, and a first inner tube ramp rearwardly adjacent said first groove, a first end of said first inner tube ramp being located at said first groove and constituting a first abutment surface, said first inner tube ramp decreasing in circumference as it extends towards said rear end of said inner tube member, wherein said shoulder subscribes a larger cross-section area through said inner tube member than said first inner tube ramp, and said shoulder terminates at its front end in a second abutment surface,
said second locking means is comprised of a protrusion and first and second ramps located towards said rear end of said outer shield member, said first and second ramps extending inwardly from said inner surface of said outer shield member, and subscribing smaller cross-sectional areas as they extend toward said rear end, said first ramp being forward of said second ramp and terminating in a third abutment surface, said second ramp terminating in said protrusion, said first ramp at said third abutment surface subscribing a substantially larger diameter than said second ramp at said protrusion.

24. A medical device according to claim 23, wherein:
said inner surface of said shield member further includes engaging means for disengageably engaging said first locking means such that when said outer shield member is engaged with said inner tube member in said retracted position the sharp end of the hollow needle is exposed and such that an application of a differential axial force on said outer shield member relative to said inner tube member will cause said engaging means and said first locking means to disengage,
said engaging means is comprised of a second inner tube ramp, a fourth abutment surface, and a second groove, said second groove rearward of said circumferential first groove and located substantially toward the rear end of said inner tube member and terminating at its front end in said second inner tube ramp, said second inner tube ramp increasing in circumference as it extends towards the front end of said inner tube, and terminating at its rear end in said fourth abutment surface.

25. A medical device according to claim 24, wherein:
said ratchet teeth are disposed in said second groove, and said ratchet notches are disposed at said protrusion.

26. A medical device according to claim 25, wherein:
said ratchet teeth are ramped ratchet teeth which increase in diameter as they extend toward said rear end of said inner tube member, and
said protrusion is a ramped notched protrusion, where said notches increase in diameter as they extend toward said rear end of said shield member.

27. A medical device according to claim 26, wherein:
said second inner tube ramp terminates at its front end at a third inner tube ramp which decreases in circumference as it extends towards the front end of said inner tube, said third inner tube ramp terminating in a valley which is of reduced circumference relative to and which lies between said first and third inner tube ramps,
said outer shield member protrusion being slidable over said valley from said retracted position in which said engaging means engages said first locking means to said shielding position in which said outer shield member is in locking engagement with said inner tube member such that said shoulder engages said inner surface of said outer shield member between said first and second ramps, and said first abutment surface is rearward of said rear end of said shield member such that attempted movement of said inner tube member forward relative to said outer shield member is stopped by abutment of said first abutment surface and the rear end of said outer shield member, and by abutment of said second and third abutment surfaces, and attempted movement of said inner tube member backward relative to said outer shield member is stopped by abutment of said shoulder of said first locking means and said second ramp of said said second locking means.

28. A medical device according to claim 21, further comprising;
 c) a hollow needle extending in said passageway and terminating at its sharp end forward of said front end of said inner tube member.

29. A medical according to claim 21, wherein: said outer shield member includes an outer surface with a substantially flat surface, wherein said substantially flat surface is angled relative to a portion of said passageway of said inner tube member by an angle of less than ten degrees.

30. A medical device according to claim 4, wherein: said angle of less than ten degrees is between two and three degrees.

* * * * *